United States Patent

Hunter et al.

[11] Patent Number: 5,486,109
[45] Date of Patent: Jan. 23, 1996

[54] CLINICAL APPLIANCE AND HANDLE

[76] Inventors: Kelly A. Hunter; Frank Hunter, both of 93 Ocean View Drive, Terrigal, New South Wales 2260, Australia

[21] Appl. No.: 218,371

[22] Filed: Mar. 25, 1994

Related U.S. Application Data

[62] Division of Ser. No. 941,128, Dec. 22, 1992, Pat. No. 5,322,437.

[30] Foreign Application Priority Data

May 7, 1990 [AU] Australia ................... PK0009

[51] Int. Cl.⁶ .................. A61C 19/04; A61C 3/00
[52] U.S. Cl. .................. 433/72; 33/513
[58] Field of Search .............. 433/72, 75, 141; 128/776, 777; 33/511, 512, 513, 514, 556, 559

[56] References Cited

U.S. PATENT DOCUMENTS

| | | | |
|---|---|---|---|
| 3,935,640 | 2/1976 | Cohan | 433/75 |
| 4,203,223 | 5/1980 | Lantenschlager et al. | 433/75 |
| 4,768,952 | 9/1988 | Loenenthal | 433/72 |
| 4,995,403 | 2/1991 | Bechman et al. | 433/72 X |
| 5,000,683 | 3/1991 | Broch | 433/72 |
| 5,028,234 | 7/1991 | Schweitzer et al. | 433/147 |
| 5,090,902 | 2/1992 | Lemon et al. | 433/72 |
| 5,112,226 | 5/1992 | Lemon et al. | 433/72 |
| 5,137,447 | 8/1992 | Hunter | 433/72 |
| 5,178,537 | 1/1993 | Currie | 433/72 |
| 5,193,999 | 3/1993 | Staubli | 433/72 |

FOREIGN PATENT DOCUMENTS 8804159  6/1988  European Pat. Off. ............ 433/72

*Primary Examiner*—Nicholas D. Lucchesi
*Attorney, Agent, or Firm*—Christie, Parker & Hale

[57] ABSTRACT

A clinical appliance (10) which is useful for taking samples from a tissue or a tissue associated material is disclosed. The appliance (10) has a head (13), and a handle (11) and a pressure sensitive element which comprises the head (13) and the handle (11) attached by a resiliently deformable member (12), and an instrument (140 retained in the head. Marks (21) are provided respectively on the head (13) and the handle (11) to indicate that when the marks are aligned a selected force is being exerted on the instrument (14). A portion of the instrument (14) consists of a needle member for probing periodontal pockets.

5 Claims, 6 Drawing Sheets

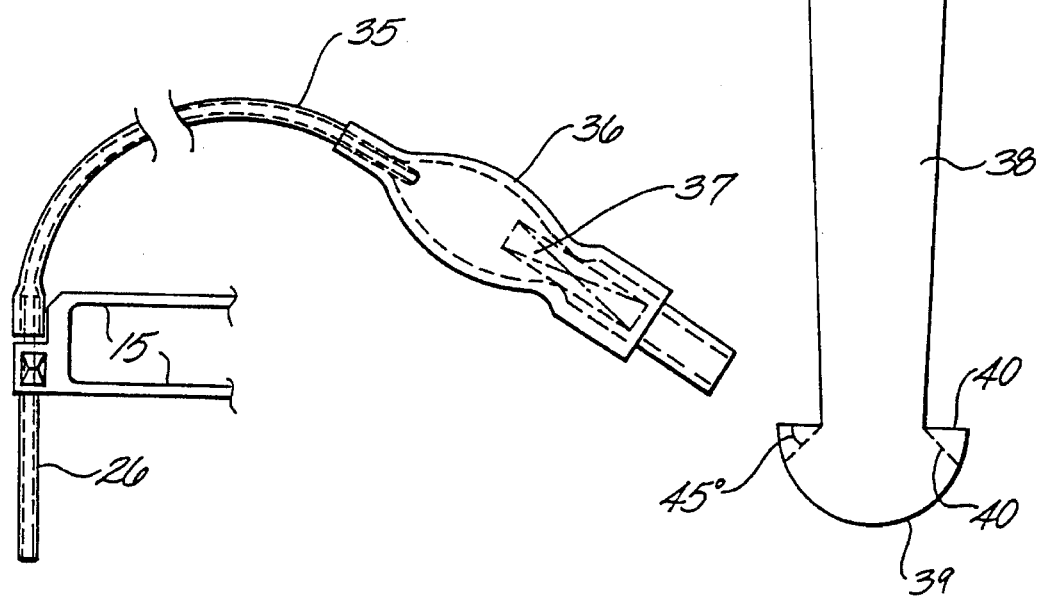

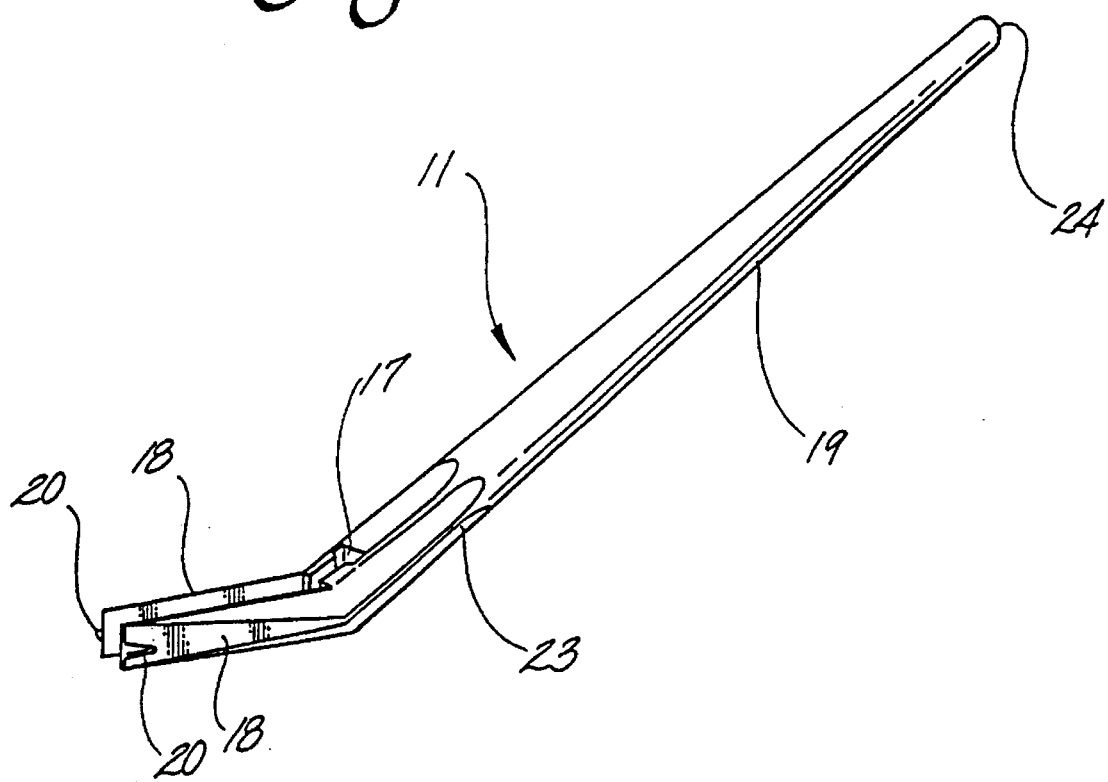

CLINICAL APPLIANCE AND HANDLE

CROSS-REFERENCE TO RELATED APPLICATIONS

This is a continuation-in-part of application Ser. No. 07/941,128, filed Dec. 22, 1992 now U.S. Pat. No. 5,322, 437.

TECHNICAL FIELD

This invention relates to an instrument design which provides a system of various or multiple procedures which may be used to advantage either separately, in any combination, in sequence or in total during many of the various health care procedures involved in any of the disciplines within either human or veterinary dentistry, medicine and or surgery.

In particular, the invention provides a universal handle which supports a series of various heads which may be disposable, pressure sensitive, rigid or sterilisable. These are each capable of executing one or more particular procedures necessary in the provision of various health care modalities.

BACKGROUND ART

In the copending International patent application PCT/AU89/00402, there is disclosed a probe adapted for use as a clinical measuring instrument or gauge. This probe comprises a needle member, an upper end of which is mounted in a head, and a handle attached to the head by a resiliently deformable member, said head and said handle each having a mark thereon which when no force is exerted on the needle member are out of alignment but when a selected force is applied, will be aligned.

The probe disclosed therein is said, inter alia, to be useful in determining periodontal pocket depths, degree of gum recession, level of tooth attachment and other oral clinical criteria. It is also said to be useful in the determination of the health of tissue other than those of the oral cavity.

In all cases, the probe of the aforementioned invention has as an essential feature, a needle member which is applied to tissues at an accurate, predetermined and reproducible force. The present inventor has found that the needle member and disposable head described therein have particular advantage whilst being used to measure clinical criteria referred to at a particular force. This attachment quickly, simply and readily allows the operator to measure many features and detect the presence or absence of infection, inflammation or disease present in that tissue by inducing a bleeding reaction from that tissue. For example, if the tissue bleeds in response to say a 0.5 mm probe at say 20 g force, then there is disease, infection or inflammation present in that tissue.

However, once the operator has identified or determined that disease or infection is present, it is useful to be able to quantify the degree, identify the type and determine the severity of the disease process. Without this information, the mere recognition of disease becomes less meaningful. It therefore follows that an operator should be able to investigate, sample or treat the site so as to determine the extent and type of disease present.

The present inventor has realised that it would be of considerable advantage to be able to readily sample tissue or other material from such a site to permit analysis in a variety of ways which may include recognition, identification, diagnosis and confirmation.

Thus without detracting from the utility of this probe, the present inventor has found that the needle member of the probe may be specifically designed to provide a sampling means or be replaced by a variety of instruments that can be beneficially applied to a tissue or a tissue associated material preferably at an accurate, predetermined and reproducible force. These instruments include a series of attachments which allow such sampling and other procedures to be executed with expedience, convenience and economy.

DISCLOSURE OF THE INVENTION

Accordingly, the present invention consists in a clinical appliance for application to a tissue, or a tissue associated material comprising a head, a handle and a pressure sensitive means which comprises the attachment of the head and the handle by a resiliently deformable member, and an instrument adapted to be retained in said head, said head and said handle each having a mark thereon which when no force is exerted on the instrument are out of alignment, but when a selected force is exerted will be aligned, said instrument having a portion for application to a tissue or tissue associated material.

In an alternative embodiment, the clinical appliance of the invention instead of having the marks on the head and handle for determining when a selected force is exerted on the instrument, electrical contact means are used whereby a contact is provided on each of the head and the handle, both contacts being connected through an electrical circuit which includes at least one of a computer, a recording means, an audio means or a visual means each of which is activated when the contacts are closed. The circuit may either be battery powered with the battery self-contained in the appliance or can be connected by leads to an external source of power. Suitable visual means may comprise a light disposed within the appliance or externally so as to be readily visible to an operator. Suitable audio means may comprise a buzzer or beeper disposed in or external to the appliance. Suitable recording means may comprise a chart recorder or a computer connected through external leads to the appliance.

It will of course be realised that a combination of recording means and audio/visual means may be used so as to both provide a clear indication to an operator that a selected pressure has been reached whilst recording that information using, for example, a computer.

The contact means may be disposed either above or below the head.

In one preferred embodiment, the head may be integrally formed with the resiliently deformable member in a manner such that it is capable of being removably attached to the handle. In this way, the head is rendered disposable which is of course important in reducing the transfer of infection or disease.

To achieve a satisfactory design in this embodiment, desirably the head, resiliently deformable member and handle will be formed from synthetic plastics material. The type of plastic may be selected on the basis of whether the components are to be capable of autoclaving, single steam, chemical or radiation sterilization, capable of repeat sterilization, or be disposable.

It will be appreciated, however, that other materials, such as metal may be used.

One means of rendering the head and resiliently deformable member detachable from the handle is described in PCT/AU89/00402 and illustrated in FIGS. 6, 8 and 11.

The instrument to be applied to a tissue may include a variety of apparatus for use in any of the following clinical situations:

(1) examination of tissue (2) measurement of tissue status or integrity (3) identification of either healthy or diseased sites (4) identification and/or diagnosis of the disease processes (5) sampling of tissue, fluid or matter from any site (6) treatment—active such as surgery or positive placement, implants etc
—passive i.e. palliative, sedative investigative (7) Therapeutic applications such as antibiotics, anti-inflammatory medicaments of any kind, irrigants, toiletry or debridement (8) Surveillance—assessment of tissue, material or disease status on an occasional, regular or incidental basis (9) Adjunctive—fibre optics
—lasers
—imaging e.g. using isotopes and the like.

(10) Any other procedures which relate to the examination, maintenance or provision of health care services or requirements, within these domains of health care.

One particularly useful class of apparatus are instruments for sampling. These may comprise the following embodiments:

(a) a cannula or capillary tube held at an upper end in the head whilst the lower end is adapted to be applied to a tissue, fluid or material to be sampled;

(b) the cannula or capillary tube of (a) to which is attached to the upper end a bladder, via an intermediate flexible tube to permit aspiration of a sample into the capillary tube or cannula and expression into a vial or other collection means;

(c) an elongate member adapted for absorbing and (d) an elongate member having at least one cavity therein adapted to retain a sample;

(e) an elongate member having a series of serrations or sample gathering detail along its length;

(f) a hemispherical ball tip with a biangular bevel of 0°–45° creating an equatorial ledge or rim which may be used to collect material for sampling purposes.

All of these embodiments may be formed from either metal or synthetic plastics material and may be either rigid or flexible.

Depending on the final use, these instruments may be used to sample fluids, tissue, microorganisms or any other matter.

If required, an instrument may be calibrated with increment markings to indicate depth.

The handle of the invention may comprise a handle as illustrated in FIGS. 10 and 11 of PCT/AU89/00402. However, the present invention has surprisingly found that an improved handle comprises an elongate member having a means at one end which is adapted to attach the resiliently deformable member including a head, a first portion adjacent to the one end adapted for gripping, and a second portion tapering away from said first portion to the distal end, said attachment means lying in a plane obtuse to a plane through the major axis of the handle defined by the first and second portions.

In a preferred embodiment, the attachment means comprises a pair of parallel plates distanced apart so as to permit movement of the head between them without interference if that particular head does move in use. This clearance is critical, since any excessive lateral movement of the handle will produce a detectable interference which then shows the operator that there has been a lateral force introduced which may or may not be a desirable factor. Thus the plates are so designed to offer correct orientation of the handle generally and direction of the forces applied to a particular head during use. In addition, on the external surface of each of the plates is a mark which represents a force alignment guide.

In the alternative embodiment which uses electrical contacts to determine when a selected force has been achieved, the marks may be replaced by a single electrical contact on one of the plates only.

The entire attachment lies at an obtuse angle to the first and second portions. It may vary in length from 2–2.5 cm.

The attachment means may include a shaped opening, adapted to receive the head, and disposed between the plates. This opening includes internal detail to permit convenient guiding, retention and ejection in relation to the corresponding detail of the head. Thus convenient insertion, operation and disposal of any one of a range of heads may be facilitated by this detail.

Where the attachment means joins the first portion the external surfaces of the attachment means are designed to blend with that of the first portion, through for example a hexagon transfer phase.

The first portion includes the "grip" area of the handle. Preferably this portion is designed, shaped and dimensioned to suit the common and comfortable three point pen-grip between the thumb and first two fingers. An example of this is an hexagon. It is of sufficient length to suit a range of phalangea sizes, but not long enough to offer incorrect grip location so as to compromise control, accuracy or sensitivity of the instrument. It thus represents an important control feature of the instrument and its use. The average length of this portion should be between 1.5–2.5 cm.

The second portion represents a general taper towards the end of the handle. The length of this portion desirably is such as to make contact between the tapered end of the handle and to rest it on the base of the index finger or near its basal knuckle. This also offers correct orientation and positioning of the instrument in the hand of the operator. The portion is 7–8 cm in length and tapers from dimension width not exceeding 8 mm at the junction of the first and second portions to a width not exceeding 5 mm at the distal end of the handle.

Accordingly, the overall length of the improved handle will generally be no more than 14 cm, usually 12–12.5 cm. The reason for this choice of dimensions is to ensure that the handle is correctly grasped in the gripping portion and not towards the tapered end, thereby ensuring maximum sensitivity and accuracy in use.

Desirably, the weight of the handle will be about 4–5 g.

It will be appreciated that heads may be used with the inventive handle that do not include a pressure sensitive means. Although such heads may not have the utility of the pressure sensitive heads, there will be some instances and procedures which do not require accurate control of pressure.

To ensure that the resiliently deformable member including a head is accurately received and located, the handle will preferably be positively locatable in a flat surface.

BRIEF DESCRIPTION OF THE DRAWINGS

In order to better understand the nature of the present invention, several embodiments will now be described with reference to the following drawings in which

FIG. 2f is a partial side view of another sampling instrument of the invention;

FIG. 2g is a sectional view of one form of the instrument of FIG. 2c and FIG. 2f, the section being taken on line 2g—2g in FIG. 6b;

FIG. 2h is a sectional view of another form of the instrument of FIG. 2c and FIG. 2f, the section being taken on line 2h—2h in FIG. 6d;

FIG. 2i is a partial side view of an alternative form of the sampling instrument of FIG. 2b;

FIG. 2j is an exploded partial side view of another sampling instrument; and

FIGS. 3, 4 and 5 are respectively perspective, plan and inverted plan views of a handle of the invention shown in FIG. 1;

MODES FOR CARRYING OUT THE INVENTION

Figure 1:
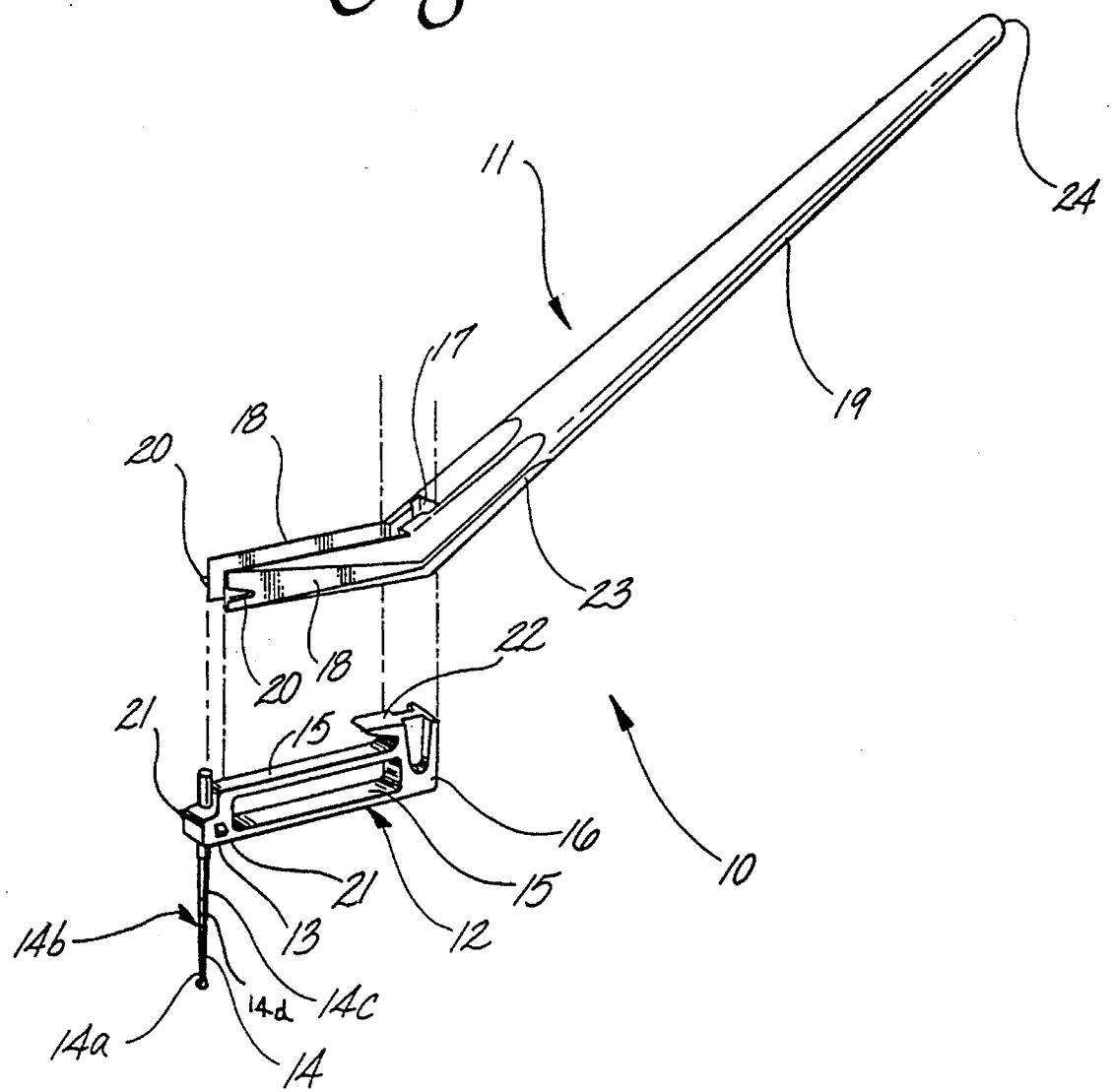
FIG. 1, are perspective views of a clinical appliance of the invention.

The clinical appliance 10 of the invention comprises a handle 11 and a removably attachable resiliently deformable member 12 and head 13. Within the head 13 is a needle member 14, substantially as described with reference to FIG. 6 of PCT/AU89/00402 with each mm calibration line 14b being a fine black line.

In the present example, a zone indicative of less than 3.5 mm depth 14a is one colour, a zone indicative of 3.5-5.5 mm depth 14d is a second contrasting colour and a third zone 14c indicative of depth greater than 5.5 mm is a third contrasting colour.

By providing contrasting colours, an operator can quickly determine the status of the probed tissue. This accords with the periodontal screening and recording system (PSR) of the American Dental Association and the American Academy of Periodontology.

Particularly preferred contrasting colours are green for the zone of less than 3.5 mm depth, orange for the 3.5–5.5 mm depth and red for the greater than 5.5 mm. These colours correspond with colours commonly used for traffic signals and in essence have corresponding meanings. That is, green is for "go", orange is for "caution" and red represents "stop" or a serious disease state.

Further, the present inventor has found the ball tip of the needle member may be designed so as to provide an effective means of sampling matter. This design includes providing a circumferential biangular bevel of between 0° and 45° to the maximum equatorial diameter.

The resiliently deformable member 12 comprises two, relatively thin parallel plates 15 connected at one end to head 13 and at the other end to a shaped portion 16 adapted to slidingly engage with a co-operating portion 17 on the handle. Adjacent portion 17 on the handle are a pair of spaced apart plates 18, each of which extends away from the handle in a plane lying at an obtuse angle to the plane of the portion of the handle shown as 19.

The plates 18 are sufficiently spaced apart to accept the resiliently deformable member 12 when slid into co-operation according to the direction of the movement indicated by the arrows in the figure.

On plates 18, there are protrusions 20 adapted to align with protrusions 21 on the head when a selected force is applied to the needle member 14.

In order to readily remove member 12 from the handle, a projection 22 is provided. Thus, by the simple action of thumb or finger pressure on 22, the member 12 is easily ejected from the handle.

The handle includes a hexagonally shaped portion 23 away from which it tapers to an end 24 about 4–5 mm in diameter.

The instruments shown in FIGS. 2a–2e are adapted to be mounted in handle 11. In each embodiment, like numerals refer to the same features described in FIG. 1.

Figure 2A:
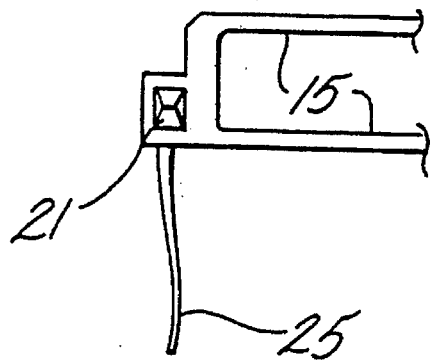
FIGS. 2a, 2b, 2c and 2d are partial side views of various sampling instruments of the invention.

In FIG. 2a, there is shown an instrument useful in examining furcations. This is achieved by providing either a rigid curved, or a flexible, deformable member.

Alternatively, this figure may represent an absorbent material such as paper, which can be placed at a site for a given time period to provide a means for collecting samples of fluid or material from that site.

This figure may also represent a non-rigid plastic material which can be used to advantage in exploring tortuous areas such as curved roots, furcations or any like curved contours.

Figure 2B:
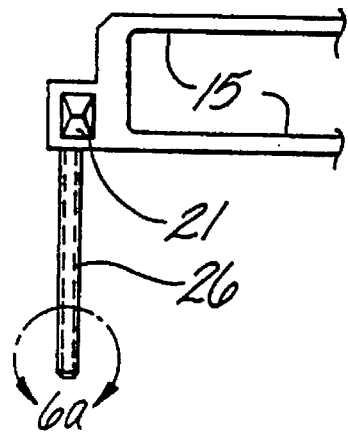

In FIG. 2b there is shown an instrument comprising a capillary tube 26 for sampling fluid material 27.

Figure 2C:
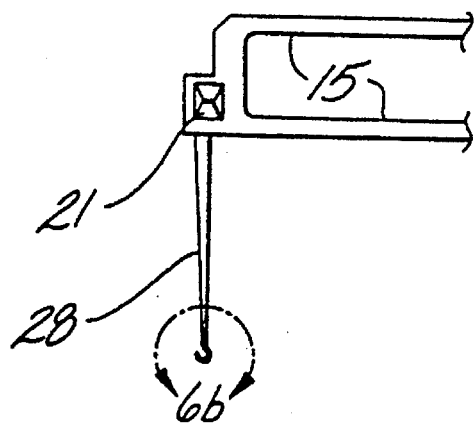

In FIG. 2c there is shown an instrument comprising an elongate metal member 28 in which there is a hook like portion 29 at a lower end adapted to sample for example matter, tissue or both. As shown in FIG. 2g, which is a sectional view through the hook like portion 29, the hook is circular in cross section and therefore may be used to sample soft, pliable materials. Alternatively, as shown in FIG. 2h, which is also a sectional view through another form of the hook like portion 29, the hook may be semi-circular in cross section with a sharp edge to define a scraping structure which may be used to advantage in shaving off or obtaining hard, adherent sample material.

Figure 2D:
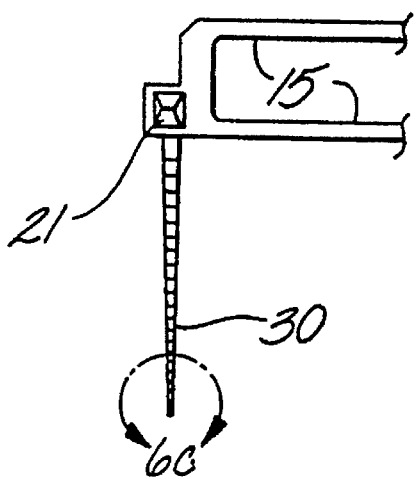

In FIG. 2d, there is shown an instrument comprising an elongate metal member 30 having a plurality of serrations 31 adapted to sample tissue, microorganisms and other material from e.g. a periodontal pocket or any other site.

Figure 2E:
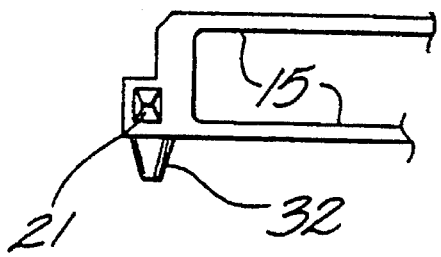
FIG. 2e is a side view of an instrument for the measurement of tooth mobility.
Figure 4:
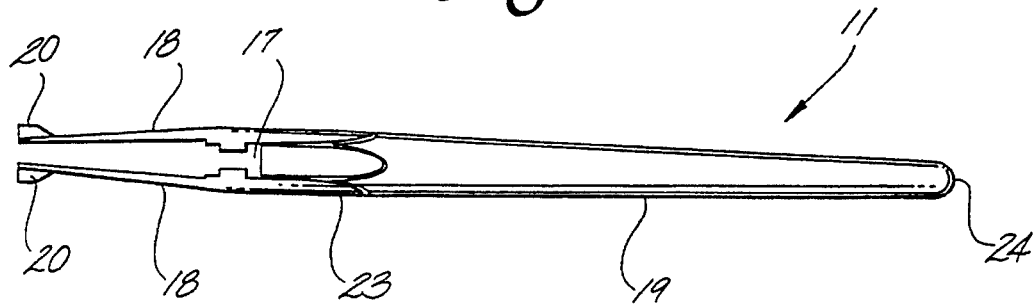
Figure 5:
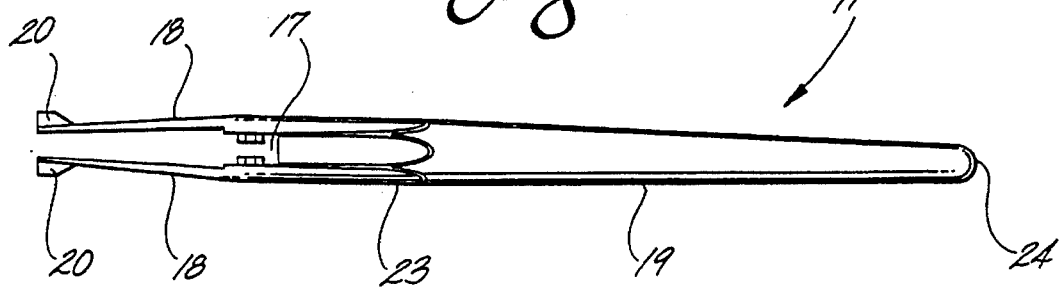
Figure 6A:
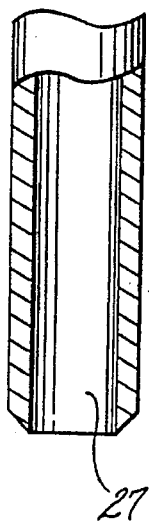
FIGS. 6a, 6b, 6c, and 6d are enlarged views of the circled portions labeled 6a, 6b, 6c, and 6d, respectively, of FIGS. 2b, 2c, 2d, and 2f, respectively.
Figure 6B:
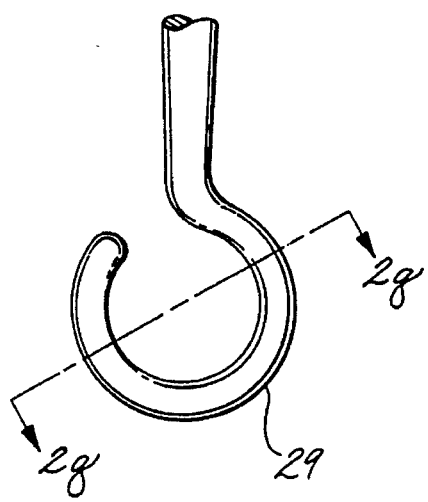
Figure 6C:
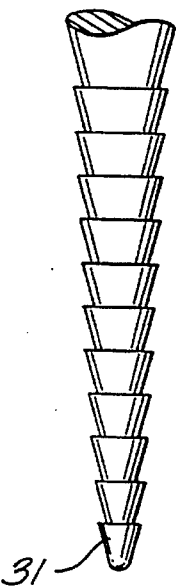
Figure 6D:
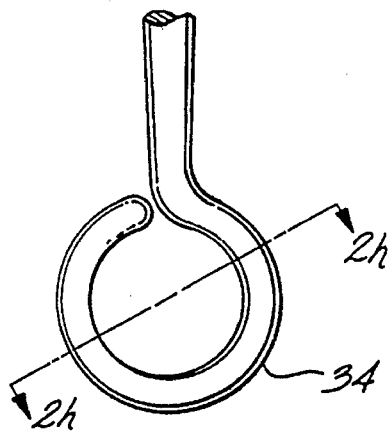

In FIG. 2e, there is shown an instrument comprising a stub 32 adapted to bear on a tooth to determine its mobility. Typically this would be done using for example a force of say 100 g to 500 g and a sliding needle arrangement to measure the tooth's displacement at that force.

In FIG. 2f, there is shown an instrument similar to that shown in FIG. 2c except that the elongate metal member 33 has a loop 34 at its lower end. As for the instrument of FIG. 2f, this instrument may be circular or semi-circular in section in the loop 34. These sections are shown in FIGS. 2g and 2h. The advantages of either circular or semi-circular section are those of the instrument of FIG. 2c with the added advantage that the loop may be capable of retaining a larger amount of sample.

In FIG. 2i, there is shown an instrument similar to that of FIG. 2b. In this example, capillary tube 26 is connected by a flexible tube 35 to a bladder 36. Using this instrument, a sample may be aspirated into the tube 26 by compressing and then gradually releasing bladder 36. Non-return valve 37 prevents the sample from being accidentally expelled.

In FIG. 2j, there is shown an instrument for sampling which comprises an elongate, solid member 38 at a lower end of which is a hemispherical ball 39. This ball has an equatorial ledge 40 which is shown as disposed at an angle of 0° or by broken lines 45° to the transverse axis of the member 38. In use, a sample of material is retained on the ledge 40.

The present inventor believes the inventive clinical appliance provides a substantial improvement over the probe disclosed in PCT/AU89/00402, particularly in view of the wider ranges of useful applications, such as in the identification, diagnosis and testing of matter. Furthermore, the handle of the present invention represents an improvement over the handle described in the aforementioned international application given the finding of the criticality of various dimensions, shapes and configurations of components thereof and its particular utility in providing a means of continued examination of tissue and material through a range of sampling, and or treatment attachments. These extend the benefit of proper scientific examinations and laboratory service to the every-day clinician. In addition, wherever the alternative embodiment of the clinical appliance is used, data can be transferred directly onto a patient's computer retained file. This has a clear benefit in enabling the clinician to access a patient's complete clinical record.

Whilst the invention described has particular advantage in the examination, measurement, assessment, diagnosis, sampling treatment, application, surveillance and adjunctive aspects of oral tissue, the same device with universal handle and the variety of interchangable attachments may similarly be used to advantage in the examination, assessment, diagnosis, sampling, treatment, application or surveillance of any other tissue, material or disease of humans or animals.

Particular advantage resides in the facility that this invention offers collection of consistent volumes of material which may be sampled. Thus particular volumes of fluid, matter or tissue may be taken through the specific dimension of each attachment together with the consistent force applied to that attachments if these are appropriate. This invention thus permits a quantitative assessment and a qualitative assessment of various criteria through the unique facility of taking consistent volumes of various samples. The volume of material gained at a particular site may be fully recovered and so will reflect the degree of disease at that site, at that time. Apart from the volumetric consistency of sampling gained within this invention, the samples thus taken may then be analysed in a variety of ways such as pathological, microbiological, histological, chemical, enzymatic, immunological or any other chosen modality appropriate in the identification, diagnosis or study of tissue, disease or material.

The current invention and in particular the handle with attachments offers the facility of various other activities as described herein to be administered such as treatment procedures which may be chosen as a result of the testing of samples taken. In summary, this invention represents a convenient and universal means of tissue examination, measurement, diagnosis, sampling, treatment surveillance, adjunctive therapy or strategies, any one of these as an individual excursion, any combination of any number of these, or the entire spectrum as chosen or intended by the operator. What the invention does is to offer a universal means of executing a variety of procedures in the health care field and a range of procedures from which may be chosen the most appropriate procedures to be executed at a site at the time with inherent accuracy, consistency, and reliability through controlled dimension and force of the instrument design. The utility of the invention resides in the facility that the operator may use any of these attachments to execute any of these procedures using the same handle either separately, in sequence, or in succession as required, or at the same time (for example, at the time of a consultation) or at subsequent or later appointments. The instrument is so designed and dimensioned to extend the consistency to any or all of these procedures and so remove the vast variables of individual operator differences and those differences observed over time.

It will be recognised by persons skilled in the art that numerous variations and modifications may be made to the invention as described above without departing from the spirit or scope of the invention as broadly described.

We claim:

1. A clinical appliance for application to a tissue, or a tissue associated material comprising a head, a handle and a pressure sensitive means which comprises the attachment of the head and the handle by a resiliently deformable member, and an instrument adapted to be retained in said head, said head and said handle each having disposed thereon a mark which when no force is exerted on the instrument are out of alignment, but when a selected force is exerted will be aligned, said instrument comprising a sampling apparatus with a portion for application to a tissue or tissue associated material, the portion being an elongate member having calibrations with increment markings to indicate depth, the increment markings defining zones therebetween, each zone having a unique color, said portion being useful for sampling tissue, fluid or other matter from said tissue or tissue associated material.

2. A clinical appliance as in claim 1 wherein the markings form three zones.

3. A clinical appliance as in claim 2 wherein a first zone indicates less than 3.5 mm depth, a second zone indicates 3.5–5.5 mm depth and a third zone indicates greater than 5.5 mm depth.

4. A clinical appliance as in claim 3 wherein the first zone is green, the second zone is orange and the third zone is red.

5. A clinical appliance as in claim 1 wherein the elongate member has a hemispherical ball tip at a lower end with a biangular bevel of from 0° to 45°, with respect to a transverse axis of said member, to create an equatorial ledge or rim.

\* \* \* \* \*